United States Patent [19]

Feiring

[11] 4,051,168
[45] Sept. 27, 1977

[54] FLUORINATION PROCESS

[75] Inventor: Andrew Edward Feiring, Wilmington, Del.

[73] Assignee: E. I. Du Pont de Nemours and Company, Wilmington, Del.

[21] Appl. No.: 685,805

[22] Filed: May 12, 1976

[51] Int. Cl.$^2$ .................. C07C 143/24; C07C 17/14
[52] U.S. Cl. .......................... 260/456 R; 260/456 P; 260/465 R; 260/465 G; 260/558 D; 260/599; 260/515 A; 260/505 R; 260/591; 260/592; 260/646; 260/556 AR; 560/8; 560/51
[58] Field of Search .............. 260/649 F, 650 F, 653, 260/456 R, 456 P, 465 R, , 465 G, 469, 558 D, 599, 515 A, 505 R, 591, 592, 646, 556 AR

[56] References Cited

U.S. PATENT DOCUMENTS

| 2,436,143 | 2/1948 | Hoehn | 260/653 |
| 2,466,189 | 4/1949 | Waalkes | 260/653 |
| 3,214,482 | 10/1965 | Caropreso et al. | 260/653 |
| 3,379,780 | 4/1968 | Robinson | 260/653 |

OTHER PUBLICATIONS

Henne et al., J.A.C.S., vol. 67, pp. 1639-1640 (1945).

Primary Examiner—James O. Thomas, Jr.
Assistant Examiner—James H. Reamer
Attorney, Agent, or Firm—Anthony P. Mentis

[57] ABSTRACT

Aromatic compounds containing an α-fluoroalkyl or α,α-difluoroalkyl side chain are prepared by reacting selected aromatic compounds with a mixture of HF and a metal oxide which is $PbO_2$ or $NiO_2$ at −30° to +80° C. Exemplary is the conversion of 4-nitrotoluene to 4-(fluoromethyl)nitrobenzene and 4-(difluoromethyl)nitrobenzene.

26 Claims, No Drawings

FLUORINATION PROCESS

BACKGROUND OF THE INVENTION

1. Field of the Invention

The invention relates to a process for replacing one or two hydrogen atoms or one hydrogen and one chlorine, bromine or iodine atom attached to a benzylic carbon atom of an aromatic compound with one or two fluorine atoms, using a mixture of hydrogen fluoride (HF) and a metal oxide which is lead dioxide ($PbO_2$) or nickel dioxide ($NiO_2$) at $-30°$ to $+80°$ C. The starting aromatic compound has one or more alkyl or halogenated alkyl or halogenated alkyl side chains and one or more electron-withdrawing groups such as nitro, carboxy, formyl and the like.

2. Prior Art

U.S. Pat. No. 2,436,143 to H. H. Hoehn discloses the reaction of a fluoroalkane containing at least two carbon atoms and from one to two fluorine atoms on a terminal carbon atom with a mixture of lead dioxide, manganese dioxide or cobaltic oxide and HF to produce a more highly fluorinated alkane. In the process the entering fluorine atom always attaches itself to the terminal carbon already bearing a fluorine atom so the resulting fluoroalkane possesses at least two fluorine atoms on the terminal carbon.

U.S. Pat. No. 2,466,189 to T. P. Waalkes, and A. L. Henne and T. P. Waalkes, *J. Amer. Chem. Soc.* 67, 1639 (1945), disclose the reaction of an olefin with lead dioxide and HF whereby two fluorine atoms are added to the double bond to produce a saturated compound.

German Offenlegungsschrift 2,140,699 uses lead dioxide and HF to add fluorine across the double bond of an olefinically unsaturated polymer.

E. R. Bissell et al., *J. Org. Chem.* 29, 1591 (1964) use lead dioxide and sulfur tetrafluoride to add fluorine across the double bond of a halogenated olefin.

U.S. Pat. No. 3,379,780 to R. E. Robinson discloses a fluorination process using HF, a oxygen-containing gas, and a noble metal of Group VIII. No lead dioxide or nickel dioxide is shown.

U.S. Pat. No. 3,214,482 to Caropreso et al. discloses ferric halide as a chlorination, bromination or iodination catalyst for hydrocarbons.

French Pat. No. 2,254,558 discloses the reaction of an aromatic compound such as $p$-$CH_3COC_6H_4NO_2$ with $MoF_6$ in the presence of $BF_3$ to produce $p$-$CH_3CF_2C_6H_4NO_2$.

None of the prior art show the present invention where one or two fluorine atoms replace one or two hydrogen atoms or one hydrogen and one chlorine, bromine or iodine atom on a benzylic carbon atom of an aromatic compound.

SUMMARY OF THE INVENTION

The invention is the fluorination process which consists essentially in reacting under essentially anhydrous conditions one mole of an aromatic compound of the formula

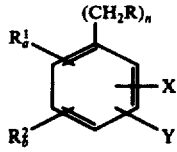

wherein
 $n$ is 1 to 3;
 $a$ and $b$ are each of 0 or 1 with the proviso that $n$ is at least 1 and the sum of $n$, $a$ and $b$ does not exceed 3;
 R is H, alkyl of 1-3 carbons or Z in which Z is F, Cl, Br or I;
 $R^1$ and $R^2$ individually are H or phenyl, or together are 1,2-phthaloyl;
 X and Y individually are H, $NO_2$, COOH, CHO, $CONH_2$, $COOR^3$, $COR^3$, $SO_3H$, $CF_3$, CN, $SO_2OR^3$, $SC_2NR_2^3$, F, Cl, Br or I,
 with the proviso that only one of X and Y can be H, F, Cl, Br or I; and
 $R^3$ is alkyl of 1-4 carbons or phenyl, with at least three moles of HF and at least one mole of a compound selected from the group consisting of lead dioxide and nickel dioxide at a temperature range of about $-30°$ to about $+80°$ C, for about 10 minutes to about 22 hours, with the proviso that when nickel dioxide is used it is the last reactant added, and recovering a fluorinated aromatic compound.

The process replaces one or two hydrogen atoms or one hydrogen and one chlorine, bromine or iodine atom attached to the benzylic carbon atom with fluorine. The product therefore contains one alpha fluorine or two alpha fluorines. In certain cases, however, where the starting material contains an alkyl side chain of more than one carbon atom, the fluorinated product may also have a fluorine atom on other carbon atoms of the alkyl side chain as well.

Where the starting material has a halogenated methyl group the only product produced contains an α,α-difluoromethyl group.

Preferred are those processes in which R is H, $CH_3$, F or Cl; $R^1$ and $R^2$ are each H; X is H and Y is $NO_2$, COOH, $CONH_2$, $COOC_2H_5$, CHO, $COC_6H_5$, CN, $SO_3H$ or $SO_2OCH_3$; and X and Y are each $NO_2$. Preferred starting materials are those where at least one of the electron-withdrawing groups is in a 1,4-relationship with the alkyl group.

The starting material has one or more alkyl or halogenated alkyl groups, as for example methyl, ethyl, fluoromethyl, chloromethyl, 1-chloropropyl, and 1-chlorobutyl, and one or more electron-withdrawing substituents such as nitro, carboxy, formyl, carboxamido, alkoxycarbonyl, alkanoyl, cyano and sulfo. These groups can be in any relationship with each other and with the alkyl or halogenated alkyl group, as for example, 1,2-, 1,3- and 1,4-., The 1,4- isomers are preferred. Starting materials which can be mentioned are:

2-, 3-, and 4-nitrotoluene
2-, 3-, and 4-methylbenzoic acid
2-, 3-, and 4-methylbenzaldehyde
2-, 3-, and 4-ethylnitrobenzene
2-, 3-, and 4-propylnitrobenzene
2-, 3-, and 4-butylnitrobenzene
2-, 3-, and 4-ethylbenzoic acid
2-, 3-, and 4-propylbenzoic acid
2-, 3-, and 4-butylbenzoic acid
2-, 3-, and 4-ethylbenzaldehyde
2-, 3-, and 4-propylbenzaldehyde
2-, 3-, and 4-butylbenzaldehyde
2-, 3-, and 4-methylbenzamide
2-, 3-, and 4-ethylbenzamide
2-, 3-, and 4-propylbenzamide
2-, 3-, and 4-butylbenzamide
ethyl 2-, 3-, and 4-methylbenzoate butyl 2-, 3-, and 4-methylbenzoate
2-, 3-, and 4-(chloromethyl)nitrobenzene
2-, 3-, and 4-(fluoromethyl)nitrobenzene
2-, 3-, and 4-(bromomethyl)nitrobenzene
2-, 3-, and 4-(iodomethyl)nitrobenzene
2-, 3-, and 4-(1-chloroethyl)nitrobenzene
2-, 3-, and 4-(1-chlorobutyl)nitrobenzene
2-, 3-, and 4-methylbenzophenone
2-, 3-, and 4-butylbenzophenone
2-, 3-, and 4-toluenesulfonic acid
methyl 2-, 3-, and 4-toluenesulfonate
butyl 2-, 3-, and 4-toluenesulfonate
t-butyl 4-toluenesulfonate
phenyl 2-, 3-, and 4-toluenesulfonate All isomers of dinitrotoluene and dimethylnitrobenzene are operative, with 2,4-, 2,6-, and 3,4-dinitrotoluene and 3,5-dimethylnitrobenzene being preferred.

The fluorination process can occur over a wide range of molar ratios of the reactants but it is preferred to use at least three moles of HF per mole of starting aromatic compound since that amount appears to be needed to introduce one molar equivalent of fluorine into the starting aromatic compound. Any amount over three molar equivalents can be used, however, and that excess will act as a solvent for the reaction. An amount of HF which is 2 to 20 times the weight of the metal oxide is preferred since it allows efficient mixing of the reactants. A portion of the excess HF may be replaced with an inert solvent such as dichloromethane chloroform, carbon tetrachloride, trichlorofluoromethane, dichlorodifluoromethane and chlorotrifluoromethane.

One mole of metal oxide is required for each molar equivalent of fluorine which is to be introduced into the starting compound. With nonstoichiometric quantities of metal oxide the reaction will proceed until all the metal oxide is consumed but it is preferred to use an excess to maximize the yield of product.

Nickel dioxide can be prepared by the procedure of K. Nakagawa et al., *J. Org. Chem.* 27, 1597 (1962).

It is advantageous to carry out the reaction under substantially anhydrous conditions since the presence of any appreciable amount of water will reduce both the conversion and yield of product. The reaction vessel is constructed from materials which are resistant to the action of hydrogen fluoride; examples include metal alloys such as Hastelloy, and plastics such as polyethylene, polypropylene, polychlorotrifluoroethylene, and polytetrafluoroethylene. For reactions at temperatures below the boiling point of hydrogen fluoride (19.5° C), the reaction vessel can be closed or open to the atmosphere if provisions to exclude moisture are taken. For reactions at temperatures at or above the boiling point of hydrogen fluoride, a closed vessel is used to minimize the loss of hydrogen fluoride.

Pressure is not critical. Atmospheric and autogenous pressures are the most convenient and are therefore preferred.

In general, the reaction is conducted by introducing the lead dioxide and starting aromatic compound into a reaction vessel of the type described above. The reaction vessel is cooled and the required amount of hydrogen fluoride is condensed in the vessel. The vessel may be evacuated prior to the introduction of hydrogen fluoride and cooled in dry ice or liquid nitrogen to facilitate collection of the hydrogen fluoride. Nickel dioxide, when used in the reaction is very highly reactive and must therefore be the last reactant added in order to insure production of the desired product. Undesirable side reactions will occur otherwise. The contents of the vessel are raised to the appropriate reaction temperature and agitated by shaking or stirring for a length of time sufficient to cause the desired reaction to occur. The reaction time and temperature necessary to obtain complete conversion to the products of the reaction can be determined by monitoring the composition of aliquots of the reaction mixture. Each aliquot is dissolved in dichloromethane, quenched with sodium fluoride, and analyzed by well-known techniques, such as gas-liquid partition chromatography (glpc, preferred method), fluorine nuclear magnetic resonance spectroscopy (19F nmr), and proton nuclear magnetic resonance spectroscopy (¹H nmr). The reaction time can be from about 10 minutes to about 22 hr; the preferred reaction times are from one to three hours.

The reaction can be conducted at about −30° to about +80° C and the preferred range is 0° to 25° C. At reaction temperatures above 40° C product yields decrease because of product instability.

In general, with an excess of the fluorinating agent, lower temperatures and shorter reaction times favor the formation of the monofluorinated products (Examples 3, 7, 9, 12 and 21); higher temperatures and longer reaction times favor the formation of the difluorinated products (Examples 1, 2, 4, 10 and 20).

The product or products are isolated from the reaction mixture by any of a variety of techniques. The preferred method is to evaporate the hydrogen fluoride and treat the residue with an organic solvent such as dichloromethane, ether, or acetone to dissolve the organic material and leave the metallic compound as a residual solid which can be separated by filtration or decantation of the liquid extract. The remaining traces of hydrogen fluoride can be removed by stirring the extract with powdered sodium fluoride at room temperature for 0.5-24 hr, preferably for ½ to 2 hours. The products are then obtained by evaporation of the solvent or by distillation of the extract, and they can be purified by the usual techniques of distillation, recrystallization, column, or preparative gas-liquid chromatography.

In a few cases, part of the initial difluoromethyl product of the reaction undergoes hydrolysis to the corresponding aldehyde in the hydrogen fluoride medium containing water generated by the fluorination reaction, thus:

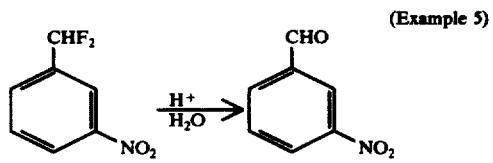

(Example 5)

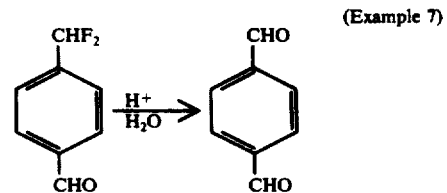

(Example 7)

The isolation and identification of such aldehyde products constitutes chemical evidence for the formation of the difluoromethyl compound (see for example, W. A. Sheppard and C. M. Sharts, "Organic Fluorine Chemistry", p. 349, W. A. Benjamin, New York, N. Y. (1969), and W. R. Hasek, W. C. Smith and V. A. Engelhardt, *J. Amer. Chem. Soc.* 82, 543 (1960)).

EMBODIMENTS OF THE INVENTION

The following illustrative examples demonstrate ways of carrying out the invention. All parts and percentages are by weight, and all temperatures are Centigrade, unless otherwise stated. Fluorine nuclear magnetic resonance chemical shifts are in parts per million from internal fluorotrichloromethane, and proton nuclear magnetic resonance chemical shifts are in part per million from internal tetramethylsilane; the solvent was deuteriochloroform (CDCl$_3$) unless otherwise stated. The density of liquid hydrogen fluoride at 19.5° C is 0.991 g ml$^{-1}$, so volume or weight can be used essentially interchangeably in measuring quantities of this reagent.

EXAMPLE 1

4-(Fluoromethyl(nitrobenzene and 4-(Difluoromethyl)nitrobenzene from 4-Nitrotoluene

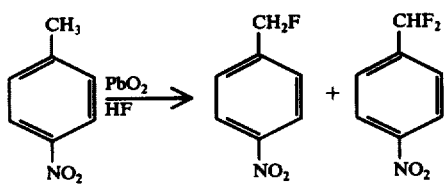

A 200-ml polychlorotrifluoroethylene vessel was charged with 5.8 g (0.024 mole) of lead dioxide and 1.37 g (0.01 mole) of 4-nitrotoluene. The vessel was evacuated and cooled in liquid nitrogen to facilitate entry of the HF. Two moles (40 ml) of hydrogen fluoride were condensed into the reaction vessel. Nitrogen was admitted to the vessel until atmospheric pressure was reached and the vessel was closed. The mixture was allowed to warm to room temperature and was stirred with a magnetic stirring bar. After 17 hr the remaining hydrogen fluoride was removed by aspirator vacuum. The residue was washed from the reaction vessel with 5 × 75-ml portions of dichloromethane. The combined dichloromethane solutions were treated with sodium fluoride powder to remove traces of hydrogen fluoride, filtered and concentrated on a rotary evaporator to give a dark oil weighing 1.52 g. Distillation of the oil at 140° bath temperature (2 mm) gave 1.14 g of faintly yellow oil. The product was analyzed by comparison with authentic samples by glpc using a 6 ft × ⅛in 10% silicone column with an oven temperature 125° and a helium carrier gas flow of 40 ml/min. The products detected (retention time and weight percent) were 4-(difluoromethyl)nitrobenzene (8 min. 71%), 4-(fluoromethyl)nitrobenzene (11.2 min, 21%), and 4-nitrobenzaldehyde (14.4 min, 8% ). The distilled product was also analyzed by fluorine and proton nmr spectroscopy:

$^{19}$F nmr, −113.5 ppm (d J = 56 Hz) CHF$_2$, and −216.8 ppm (t J = 48 Hz) CH$_2$F; $^1$H nmr, δ 5.65 (d J = 48 Hz) CH$_2$F, and 6.73 ppm (t J = 56 Hz) CHF$_2$; these signals identify the two fluorides.

EXAMPLE 2

4-(Difluoromethyl)nitrobenzene from 4from 4-Nitrotoluene

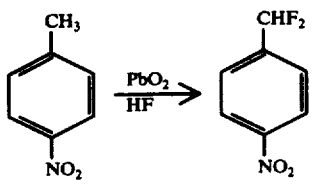

A 360-ml Hastelloy bomb tube was charged with 8.2 g (0.06 mole) of 4-nitrotoluene and 52.0 g (0.218 mole) of lead dioxide. The bomb was cooled in a dry ice and acetone mixture, evacuated and charged with 150 g of hydrogen fluoride. The bomb tube was agitated for 17 hr with an inside temperature of 30°-46° C. The hydrogen fluoride was removed using an aspirator. The residue was rinsed from the bomb with 5 × 100 ml of dichloromethane. Several hundred grams of sodium fluoride powder was added to the dichloromethane to remove residual hydrogen fluoride. The mixture was filtered, and the filtrate was concentrated on a rotary evaporator to a dark oil (10.1 g). The oil was distilled to give 7.0 g (0.04 mole, 67%) of 4-(difluoromethyl)nitrobenzene (4-nitrobenzalfluoride), bp 83° (1.9 mm), $^1$H nmr, δ 6.93 (t J = 57 Hz) CHF$_2$ and 8.18 ppm (q) C$_6$H$_4$; $^{19}$F nmr, −113.4 ppm (d J = 57 Hz) CHF$_2$.

EXAMPLE 3

4-(Fluoromethyl)nitrobenzene and 4-(Difluoromethyl)nitrobenzene from 4-Nitrotoluene The procedure of Example 1 was repeated with 2.5 g (0.01 mole) of lead dioxide and 1.4 g (0.01 mole) of 4-nitrotoluene and a 4 hr. reaction time. Glpc analysis (as in Example 1) of the crude product mixture (1.52 g) showed 4-(fluoromethyl)nitrobenzene (86%), 4-(difluoromethyl)nitrobenzene (12%) and 4-nitrobenzaldehyde (2%) to be present.

EXAMPLE 4

2-(Difluoromethyl)nitrobenzene from 2-Nitrotoluene

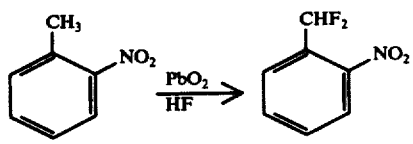

The procedure of Example 1 was repeated with 7.2 g (0.03 mole) of lead dioxide, 1.37 g (0.01 mole) of 2-nitrotoluene, and 50 ml of hydrogen fluoride. The reaction proceeded at 25° for 5 hr. The crude product was a black oil (1.2 g) which was distilled at 140° bath temperature (3 mm) to give 0.7 g of 2-(difluoromethyl)nitrobenzene (2-nitrobenzal fluoride) as a yellow oil, $^1$H nmr, δ 7.5-8.2 (m) C$_6$H$_4$ and 7.37 ppm (t J = 55 Hz) CHF$_2$; $^{19}$F nmr −115.5 ppm (d J = 55 Hz) CHF$_2$.

EXAMPLE 5

3-(Difluoromethyl)nitrobenzene, 3-(Fluoromethyl)nitrobenzene and 3-Nitrobenzaldehyde from 3-Nitrotoluene

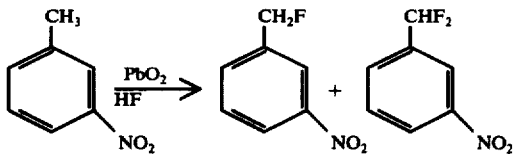

The procedure of Example 2 was repeated with 11.0 g (0.08 mole) of 3-nitrotoluene, 58.0 g (0.243 mole) of lead dioxide, and 100 g of hydrogen fluoride in a 200-ml Hastelloy bomb for 17 hr. The crude black oil obtained (9.2 g) was distilled to give 4.7 g of yellow oily distillate, bp 80°-120° (1.5 mm). Glpc analysis of the distillate (same conditions as Example 1) showed the presence of 3-(difluoromethyl)nitrobenzene (3-nitrobenzal fluoride) (6.8 min, 35%), 3-(fluoromethyl)nitrobenzene (3-nitrobenzyl fluoride) (8.8 min, 5%), and 3-nitrobenzaldehyde (15.2 min, 60%), whose identities were confirmed by gas chromatography-mass spectroscopy (gc-ms). These products were also identified by $^{19}F$ nmr $-112.66$ ppm (d) $CHF_2$ and $-213.25$ ppm (t) $CH_2f$ and by $^1H$ nmr, $\delta$ 11.7 (s) CHO, 6.80 (t) $CHF_2$, and 5.98 (d) $CH_2F$.

EXAMPLE 6

4-(Difluoromethyl)benzoic acid from 4-Methylbenzoic Acid

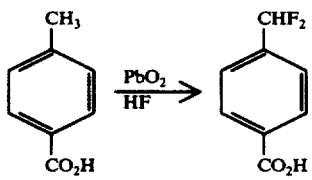

A 200-ml polychlorotrifluoroethylene vessel was charged with 1.36 g (0.01 mole) 4-methylbenzoic acid and 7.2 g (0.03 mole of lead dioxide. The vessel was evacuated, cooled in liquid nitrogen and charged with 30 ml of hydrogen fluoride. The reaction vessel was cooled in an ice-water bath and the contents were stirred for 3 hr. The hydrogen fluoride was removed by aspirator vacuum at ice-water temperature. The residue was dissolved in 400 ml. of 5% aqueous potassium hydroxide and treated with 100 ml of saturated aqueous sodium sulfide to precipitate the lead salts. The mixture was filtered, the filtrate was acidified with concentrated hydrochloric acid, and extracted with 3 × 100 ml of dichloromethane and 1 × 100 ml of ether. The combined organic extracts were dried over anhydrous magnesium sulfate and concentrated under vacuum to give 1.45 g of yellow solid. The product was analyzed by proton and fluorine nmr spectroscopy as 4-(difluoromethyl)benzoic acid and a trace of 4-formylbenzoic acid: $^{19}F$ nmr, $-112.3$ ppm (d J = 56 Hz) $CHF_2$; $^1H$ nmr, $[(CD_3)_2CO]$, $\delta$ 10.2 (s) CHO, 9.0 (broad) $CO_2H$, 7.3–8.5 (m) $C_6H_4$, and 6.97 (t J = 56 Hz) $CHF_2$.

EXAMPLE 7

4-(Fluoromethyl)benzaldehyde from 4-Methylbenzaldehyde

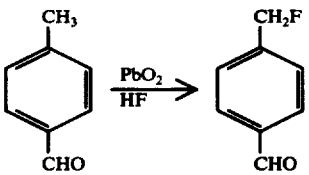

A 200 ml polychlorotrifluoroethylene vessel was charged with 1.2 g (0.01 mole) of 4-methylbenzaldehyde and 7.2 g (0.03 mole) of lead dioxide. The vessel was evacuated and cooled in liquid nitrogen. Hydrogen fluoride (30 ml) was condensed into the vessel. The vessel was brought to atmospheric pressure with nitrogen, closed, and the mixture was stirred for 2 hr at ice-water bath temperature (0°). The hydrogen fluoride was removed at this temperature using aspirator vacuum, and the residue was washed with dichloromethane. Evaporation of the dried extracts gave 1.25 g of yellow solid which contained at least four products by $^{19}F$ nmr. The experiment was repeated on twice the above scale, using 4 × 75 ml of ether to wash the residue. The ether extracts were washed with 2 × 75 ml of 5% aqueous potassium hydroxide, dried over anhydrous magnesium sulfate, and concentrated under vacuum to give 1.19 g of dark solid. Analysis by glpc (Column of Example 1 at 100°) showed that this product was a mixture of unreacted 4-methylbenzaldehyde (8.4 min, 37%), 4-(fluoromethyl)benzaldehyde (12.0 min, 53%), and terephthalaldehyde (17.6 min, 10%). These results were confirmed by: gc-ms where mass-to-charge (m/e) values of 120 for 4-methylbenzaldehyde, 138 for 4-(fluoromethyl)benzaldehyde, and 134 for terephthaldehyde were identified as the parent ions of the compounds producing the three peaks; $^1H$ nmr, $\delta$ 9.98, 10.07 and 10.17 (singlets) 3 different CHO, 7.2–8.1 (m) $C_6H_4$, 5.53 (d J = 47 Hz) $CH_2F$, and 2.40 ppm (s) $CH_3$; $^{19}F$ nmr, $-214.25$ ppm (t J =47 Hz) $CH_2F$.

The aqueous potassium hydroxide fraction from the extraction was acidified with hydrochloric acid and extracted with 3 × 75 ml of ether; evaporation of the dried extracts gave 1.89 g of dark solid acidic material, which by $^{19}F$ nmr contained 4-(difluoromethyl)benzoic acid (doublet at $-112.0$ ppm) and 4-(fluoromethyl)benzoic acid (triplet at $-217.79$ ppm) and three other unidentified components.

EXAMPLE 8

4-(1,1-Difluoroethyl)nitrobenzene, 4-(1-Fluoroethyl)-nitrobenzene, and 4-(1,2-Difluoroethyl)nitrobenzene from 4-Ethylnitrobenzene

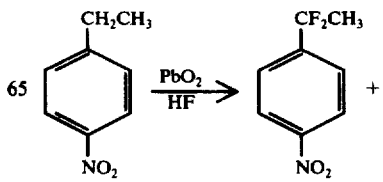

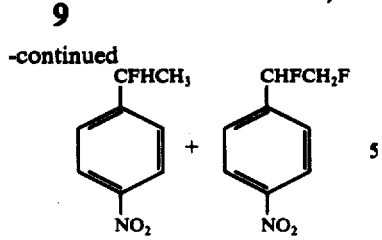

The procedure of Example 7 was followed using 1.08 g (0.007 mole) of 4-ethylnitrobenzene, 5.3 g (0.022 mole) of lead dioxide and 40 ml of hydrogen fluoride for 4 hr. The residue left after evaporation of the hydrogen fluoride was extracted with 5 × 100 ml of dichloromethane, and filtered. The combined extracts were treated with sodium fluoride powder, filtered, and concentrated to a dark oil (0.97 g). This was combined with 2.2 g from another larger-scale experiment which had been run for 2 hr, and distilled at 140° bath temperature (1.5 mm). The product (2.3 g) was analyzed by glpc on a 10 ft × ¼ in 10% silicone column at 200°, and found to have four components with retention times 8.0 min (12%), 12.8 min (36%), 25.2 min (46%), and 29.6 min (6%). The three major components were separated by preparative glpc under the same conditions, and were identified by proton and fluorine nmr. The 8.0-min material was 4-(1,1-difluoroethyl)nitrobenzene, $^{19}$F nmr, −89.54 ppm (q J = 18 Hz) CF$_2$; $^1$H nmr, δ 2.0 (t J = 18) CH$_3$, and 8.0 ppm (q) C$_6$H$_4$; the 12.8-min material was 4-(1-fluoroethyl)nitrobenzene, $^{19}$F nmr, −173.2 ppm (6-line pattern, $J_{HF}^{vic}$ = 48 Hz, and $J_{HF}^{gem}$ = 24 Hz) CHF; the 25.2-min material was 4-(1,2-difluoroethyl)nitrobenzene, $^{19}$F nmr, −190.55 ppm (10-pattern, $J_{FF}$ = 14 Hz, $J_{HF}^{vic}$ = 48 Hz, $J_{HF}^{gem}$ = 18 Hz) CH$_2$F, and −227.08 ppm (12-line pattern, $J_{FF}$ = 14 Hz, $J_{HF}^{vic}$ = 47 Hz, $J_{HF}^{gem}$ = 18 Hz).

EXAMPLE 9

4-(Fluoromethyl)benzamide from 4-Methylbenzamide

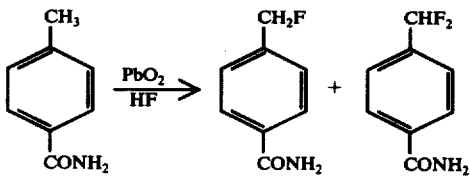

A 200ml polychlorotrifluoroethylene vessel was charged with 1.35 g (0.01 mole) of 4-methylbenzamide and 7.2 g (0.03 mole) of lead dioxide. The vessel was evacuated, cooled in liquid nitrogen, and charged with 30 ml of hydrogen fluoride. The reaction vessel was immersed in an ice bath and the contents were stirred for 4 hr. The hydrogen fluoride was removed by aspirator vacuum. The residue in the flask was triturated with ether. The ether solution was washed with water, dried over anhydrous magnesium sulfate, and evaporated to give 0.66 g of colorless solid. The experiment was repeated with 1.45 g (0.011 mole) of 4-methylbenzamide and acetone extraction of the metallic residues to give 1.60 g of yellow solid, identified as 4-(fluoromethyl)benzamide, $^1$H nmr (acetone-d$_6$) δ 5.53 (d J = 47 Hz) CH$_2$F, 7.83 (q) C$_6$H$_4$, and 8.17 ppm (bs) NH$_2$; $^{19}$F nmr (acetone-d$_6$) −212.44 ppm (t J =47 Hz) CH$_2$F. The $^{19}$F nmr also revealed the presence of 10% of 4-(difluoromethyl)benzamide at −111.73 ppm (d J = 48 Hz) CHF$_2$.

EXAMPLE 10

Ethyl 4-(Difluoromethyl)benzoate from Ethyl 4-Methylbenzoate

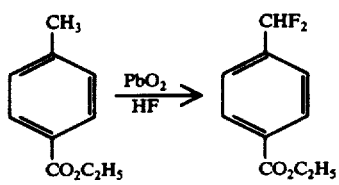

The procedure of Example 9 was used with ethyl 4-methylbenzoate (1.64 g, 0.01 mole), lead dioxide (7.2 g, 0.03 mole) and hydrogen fluoride (30 ml) with a 4-hr reaction time. The metallic residue was extracted with 3 × 75-ml of ether, filtered, and the combined ether extracts were washed with 5% aqueous potassium hydroxide and dried over anhydrous magnesium sulfate. Removal of the ether under vacuum gave a pale yellow oil (1.75 g). Glpc analysis (as in Example 1, at 120° ) showed two major and four minor peaks. Material obtained when the experiment was repeated for 1 hr reaction time showed peaks at 12 min (79%) and 25.6 min (21%). The 12-min peak was identified by gc-ms as ethyl 4-(difluoromethyl)benzoate m/e 200; $^{19}$nmr -112.71 ppm (d J = 56 Hz) CHF$_2$. Quantitative glpc analysis using 2-nitrotoluene as the internal standard indicated that the yield of ethyl 4-(difluoromethyl)benzoate was 18%, based upon ethyl 4-methylbenzoate.

EXAMPLE 11

4-(Fluoromethyl)nitrobenzene and 4-(Difluoromethylnitrobenzene from 4-Nitrotoluene

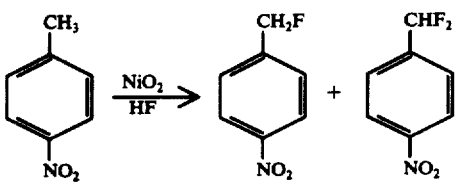

A 300-ml polytetrafluoroethylene vessel was charged with 1.37 g (0.01 mole) of 4-nitrotoluene. The vessel was evacuated, cooled in liquid nitrogen, and charged with 50 ml of hydrogen fluoride. The vessel was connected by a T-tube and mercury bubbler to a source of nitrogen, and immersed in a dry ice and acetone bath. Nickel dioxide (8.0 g, activity 3.96 × 10$^{-3}$ g-atom O$_2$/g by iodometric titration (0.032 mole)) was added in several portions over 15 min, and the reaction vessel was sealed and allowed to warm to room temperature. This order of addition was used because mixing nickel dioxide with 4-nitrotoluene without hydrogen fluoride as solvent caused in immediate reaction to unknown products. After the mixture had stirred for 18 hr, the hydrogen fluoride was removed with aspirator vacuum, and the residue was triturated with 300 ml of dichloromethane, and filtered. The filtrate was treated with sodium fluoride powder to remove traces of hydrogen fluoride, filtered, and concentrated under vacuum to give 1.4 g of solid. This material was analyzed by glpc as in Example 1, and found to contain 34% of 4-(difluoromethyl)nitrobenzene, 60% of 4-(fluoromethyl)nitrobenzene, 6% of 4-nitrotoluene, and 4% of 4-nitrobenzaldehyde. The $^{19}$F nmr spectrum showed a doublet at −112.92 ppm (CHF$_2$) and a triplet at −215.72 ppm (CH$_2$F) with an integration ratio of 1:2.1.

EXAMPLE 12

3,4-Dinitro(fluoromethyl)benzene (3,4-Dinitrobenzyl)Fluoride) from 3,4-Dinitrotoluene

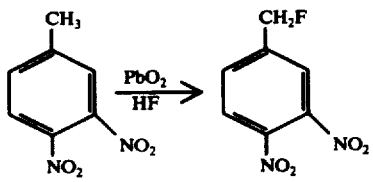

A 200-ml polychlorotrifluoroethylene vessel was charged with 1.82 g (0.01 mole) of 3,4-dinitrotoluene and 7.2 g (0.03 mole) of lead dioxide. The vessel was evacuated, cooled in liquid nitrogen, and charged with 30 ml of hydrogen fluoride. The vessel was sealed, warmed to room temperature, and the contents were stirred for 1 hr. The hydrogen fluoride was removed by aspirator vacuum. The residue was triturated with 300 ml of ether and filtered through a bed of anhydrous magnesium sulfate. The filtrate was washed with 5% aqueous potassium hydroxide, dried with anhydrous magnesium sulfate, and concentrated in vacuo to 1.72 g of yellow oily solid. The solid was dissolved in 25 ml of boiling carbon tetrachloride and cooled in an ice and salt bath to give 1.5 g (0.0075 mole, 75%) of 3,4-dinitro(-fluoromethyl)benzene (3,4-dinitrobenzyl fluoride) as pale yellow cystals with mp 37.5°-38.5°, and $^1$H nmr, δ 5.62 (d J = 46 Hz) CH$_2$F, and 7.7-8.2 ppm (m) C$_6$H$_3$, and $^{19}$F nmr, −218.98 ppm (t J = 46Hz) CH$_2$F.

EXAMPLE 13

4-(Difluoromethyl)nitrobenzene from 4-(Chloromethyl)nitrobenzene

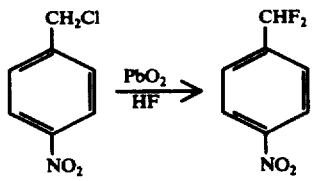

The procedure of Example 1 was followed with 4-(chloromethyl)nitrobenzene(1.72 g, 0.01 mole), lead dioxide (7.2 g, 0.03 mole) and hydrogen fluoride (50 ml) for 22 hr at room temperature to give 1.68 g of crude product as a yellow oily solid. This was analyzed by proton nmr, and glpc (as in Example 1) and shown to be a mixture of 4-(difluoromethyl)nitrobenzene (79%) and 4-nitrobenzaldehyde (11%).

EXAMPLE 14

4-(Difluoromethyl)benzophenone from 4-Methylbenzophenone

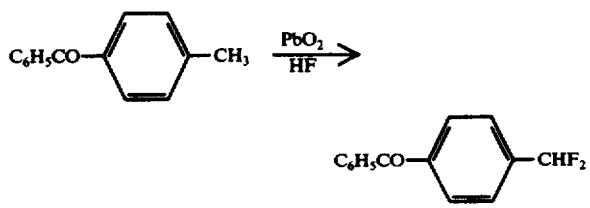

The procedure of Example 12 was followed using 1.96 g (0.01 mole) of 4methylbenzophenone, 7.2 g (0.03 mole) of lead dioxide, and 30 ml of hydrogen fluoride, to give 2.0 g of dark oil. Glpc analysis (as in Example 1, at 200°) showed two products to be present with retention times of 8.0 and 10.8 min. The crude product was chromatographed on 60 g of silica gel. Elution with 25% ether in petroleum ether, using glpc to monitor the elution, gave: (1) 0.90 g (38%) of 4-(difluoromethyl)-benzophenone, mp 71.5°-73°, $^1$H nmr, δ 6.73 (t J = 57 Hz) CHF$_2$, and 7.2-8.0 ppm (m) 9 aromatic protons, $^{19}$F nmr −112.67 ppm (d J = 57 Hz) CHF$_2$, and (2) 0.6 g (28%) of 4-(fluoromethyl)benzophenone, $^1$H nmr, δ 5.43(d J = 47 Hz) CH$_2$F and 7.2-8.0 ppm (m) 9 aromatic protons, $^{19}$F nmr, −212.98 ppm (t) CH$_2$F.

EXAMPLE 15

4-(Difluoromethyl)benzonitrile from 4Methylbenzonitrile

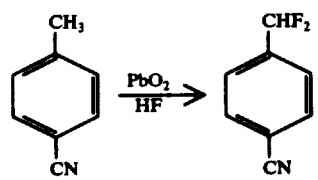

The procedure of Example 12 was followed using 1.17 g (0.01 mole) of 4-methylbenzonitrile, 7.2 g (0.03 mole) of lead dioxide, and 30 ml of hydrogen fluoride, to give 0.93 g of faintly yellow oil. Glpc analysis (as in Example 1), showed a single peak with retention time of 6 min. The crude product was short-path distilled to give 0.70 g (45%) of 4-(difluoromethyl)benzonitrile, bp 63°-65° (0.7 mm); $^1$H nmr, δ 6.75 (t J = 57 Hz) CHF$_2$ and 7.75 ppm (d) C$_6$H$_4$; $^{19}$F nmr, −113.64 ppm (d) CHF$_2$; ir, ν$_{max}$(neat) 2250 cm$^{-1}$ (CN).

EXAMPLE 16

4-(Fluoromethyl)benzenesulfonyl Fluoride and 4-(Difluoromethyl)benzenesulfonyl Fluoride from 4-Toluenesulfonic Acid

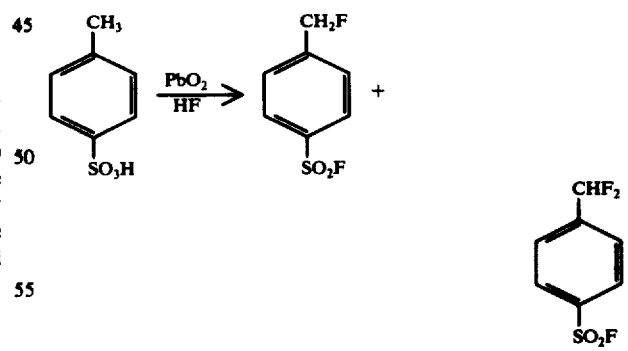

A 200-ml polychlorotrifluoroethylene vessel was charged with 1.7 g (0.01 mole) of 4-toluenesulfonic acid and 7.2 g (0.03 mole) of lead dioxide. The vessel was evacuated, cooled in liquid nitrogen and charged with 40 ml of hydrogen fluoride. The vessel was sealed and the contents were allowed to warm to room temperature. After the mixture had stirred overnight the hydrogen fluoride was removed on the aspirator. The residue was triturated with 3 × 100 ml ether and filtered. The filtrate was concentrated under vacuum to give 0.7 g of an oil. The oil was analyzed by proton and fluorine nmr and found to be a mixture of 1 part 4-(fluoromethyl)benzene-sulfonyl fluoride and 1.2 parts 4-(difluoromethyl)-benzene-sulfonyl fluoride; $^1$H nmr, δ 5.53 (d J = 47 Hz) CH$_2$F, 6.77 (t J = 57 Hz) CHF$_2$, and 7.5–8.4 ppm (2 q) C$_6$H$_4$; $^{19}$F nmr, −218.32 (t) CH$_2$F, −114.28 ppm (d) CHF$_2$, and −65.0 ppm (s) SO$_2$F.

EXAMPLE 17

4-(Fluoromethyl)nitrobenzene from 4-Nitrotoluene using Dichloromethane Solvent

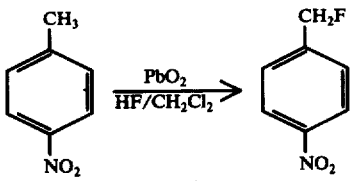

A 200-ml polychlorotrifluoroethylene vessel was charged with 5.0 g (0.021 mole) of lead dioxide, evacuated, cooled in liquid nitrogen, and charged with 15 ml of hydrogen fluoride. The system was connected to a nitrogen source using a T-tube and bubbler. The mixture was immersed in a dry ice and acetone bath, stirred, and treated with a solution of 2.8 g (0.02 mole) of 4-nitrotoluene in dichloromethane (40 ml) over 10 min. The reaction vessel was sealed and the mixture was stirred at room temperature for 16 hr. The hydrogen fluoride was vented, and the supernatant liquid was decanted from the solid. The solid was rinsed with 2 × 100 ml of dichloromethane, and the combined extracts were treated with 60 g of powdered sodium fluoride for 2 hr, filtered, and evaporated to leave 3.0 g of a brown oil. Analysis by glpc (as in Example 1) showed that this was a mixture of 25% of 4-nitrotoluene and 75% of 4-(fluoromethyl)nitrobenzene, and a trace (<1%) of 4-(difluoromethyl)nitrobenzene. This was confirmed by proton nmr, δ 2.42 (s) CH$_3$, and 5.52 and (d) CH$_2$F.

EXAMPLE 18

3-(Difluoromethyl)-5-(fluoromethyl)nitrobenzene, 3,5-bis(Fluoromethyl)nitrobenzene, and 3-(Fluoromethyl)-5-nitrobenzaldehyde from 3,5-Dimethylnitrobenzene

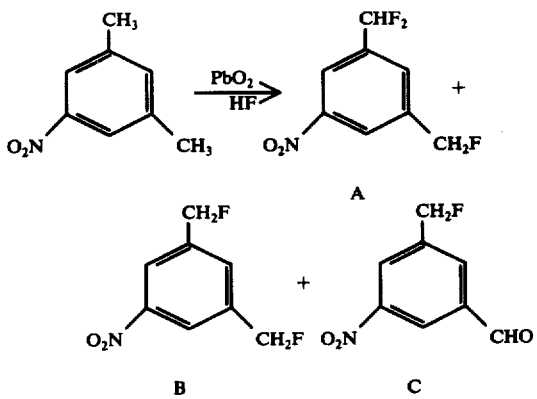

The procedure of Example 12 was followed using 1.51 g (0.01 mole) of 3,5-dimethylnitrobenzene (5-nitro-m-xylene), 7.2 g (0.03 mole) of lead dioxide and 30 ml of hydrogen fluoride to give 1.17 g of dark oil. Glpc (as in Example 1, at 140°) showed the presence of three components, A (9.8 min), B (15.6 min) and C (25.2 min) and $^{19}$F nmr showed three signals −214.26, −215.38, and −215.77 ppm for three different CH$_2$F groups in a molar ratio of 2:1.2:1. Chromatography of the crude product on 30 g of silica gel, using 20% ether in hexane as the eluant, gave, in order of elution, 0.20 g of a mixture of A and B, enriched in A, 0.31 g of a mixture of A and B, enriched in B, and 0.09 g of C. Analysis of the nmr spectra showed that (1) A was 3-(difluoromethyl)-5-(fluoromethyl)nitrobenzene, $^1$H nmr, δ 5.53 (d) CH$_2$F, 6.78 (t) CHF$_2$, 7.65 (s), 7.80 (s) and 8.27 ppm (s) C$_6$H$_3$; $^{19}$F nmr −215.03 (t) CH$_2$F and −112.89 ppm (d) CHF$_2$. (2) B was 3,5-bis(fluoromethyl)nitrobenzene, $^1$H nmr δ 5.57 (d) 2 CH$_2$F, 7.65 (s) and 8.12 ppm (s) C$_6$H$_3$; $^{19}$F nmr −213.88 ppm (t) CH$_2$F. (3) C was 3-(fluoromethyl)-5-nitrobenzaldehyde, $^1$H nmr δ 5.62 (d) CH$_2$F, 8.27 (s), 8.53 (s), and 8.67 (s) C$_6$H$_3$, and 10.18 ppm (s) CHO; $^{19}$F nmr, −215.58 ppm (t) CH$_2$F.

EXAMPLE 19

4-(Fluoromethyl)benzonitrile and 4-(Difluoromethyl)benzonitrile from 4-Methylbenzonitrile

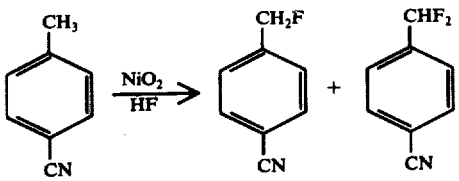

A 200-ml polychlorotrifluoroethylene vessel was cooled in liquid nitrogen, pumped down to 2 mm pressure, and charged with 50 ml of hydrogen fluoride. The vessel was flushed with nitrogen at atmospheric pressure and held at ice-bath temperature while 1.17 g (0.01 mole) of 4-methylbenzonitrile was added. Nickel dioxide (9.8 g, activity 3.12 × 10$^{-3}$ g-atom O$_2$/g, 0.031 mole) was added in small portions over 45 min, and the mixture was stirred at 0° for 3 hr. The hydrogen fluoride was removed by aspirator vacuum, and the residue was stirred with 300 ml of ether and filtered. The filtrate was washed with 5% aqueous sodium bicarbonate, dried over magnesium sulfate, and concentrated by rotary evaporator to give 1.0 g of yellow oil. This material had δ$_{max}$ 2240 cm$^{-1}$ (C≡N) and $^1$H nmr, δ8.0 − 7.1 (m) C$_6$H$_4$, 5.47 (d) CH$_2$F, and 2.43 (s) ppm CH$_3$, the ratio of starting material to 4-(fluoromethyl)benzonitrile (δ 2.43:5.47 peaks) being 1.36:1. Quantitative $^{19}$F nmr analysis using 3,4-dinitrobenzyl fluoride (Example 12) as an internal standard showed 4-(fluoromethyl)benzonitrile at −215.80 ppm (t) CH$_2$F, and 4-(difluoromethyl)benzonitrile at −113.65 ppm (d) CHF$_2$, in the ratio of 10.43:1, corresponding to 25.5% conversion to monofluoride and 2.4% conversion to difluoride.

EXAMPLE 20

4-(Fluoromethyl)nitrobenzene and 4-(Difluoromethyl)nitrobenzene from 4-Nitrotoluene

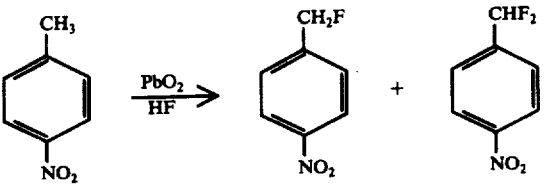

A 200-ml Hastelloy bomb tube was charged with 4.1 g (0.03mole) of 4-nitrotoluene and 21.5 g (0.09 mole) of lead dioxide. The bomb was cooled in a dry ice and acetone mixture; evacuated and charged with 75 g of hydrogen fluoride. The bomb tube was agitated for 10 minutes with an inside temperature of 80° C. After cooling to room temperature, the hydrogen fluoride was removed using aspirator vacuum. The residue was rinsed from the bomb using 4 × 100-ml portions of dichloromethane. The combined dichloromethane solutions were treated with 25 g of sodium fluoride powder, filtered and concentrated on a rotary evaporator to give a dark oil weighing 4.3 g. Distillation of the oil at 130°-140° bath temperature (1.1 mm) gave 3.0 g of golden oil. Glpc analysis (as in Example 1) showed 4-(difluoromethyl)nitrobenzene (63%), 4-(fluoromethyl)nitrobenzene (19%) and 4-nitrobenzaldehyde (18%) to be present.

EXAMPLE 21

4-(Fluoromethyl)nitrobenzene from 4-Nitrotoluene

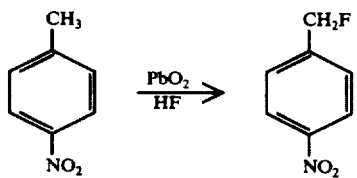

A 200-ml Hastelloy bomb tube was charged with 4.1 g (0.03 mole) of 4-nitrotoluene and 21.5 g (0.09 mole) of lead dioxide. The bomb was cooled in dry ice and acetone mixture, evacuated and charged with 75 g of hydrogen fluoride. The bomb tube was agitated for 18 hr at −30° C. The reaction mixture was poured into a polyethylene bottle which contained 200 g of ice. The bomb tube was rinsed with 2 × 200-ml portions of dichloromethane, which were added to the polyethylene bottle. The mixture was filtered and the filtrate was transferred to a polyethylene separatory funnel. The dichloromethane layer was drained off and the aqueous layer was extracted with 100 ml dichloromethane. The combined dichloromethane solutions were washed with 100 ml of saturated aqueous sodium bicarbonate solution, dried over anhydrous magnesium sulfate and concentrated under vacuum to a light brown oil weighing 4.0 g. The product was analyzed by glpc (as in Example 1) as a mixture of 4-nitrotoluene (52%) and 4-(fluoromethyl)nitrobenzene (48%). The product was also analyzed by $^1$H nmr spectroscopy δ2.45 (s), CH$_3$ and 5.65 ppm (d, J = 48 Hz) CH$_2$F.

EXAMPLE 22

4-(Difluoromethyl)nitrobenzene from 4-(Fluoromethyl)nitrobenzene

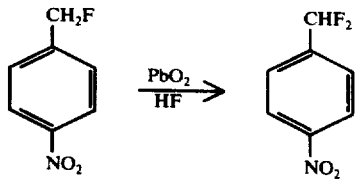

A 200-ml polychlorotrifluoroethylene vessel was charged with 0.775 g (0.005 mole) of 4-(fluoromethyl)nitrobenzene and 2.39 g (0.01 mole) of lead dioxide. The vessel was evacuated, cooled in liquid nitrogen and charged with 25 ml hydrogen fluoride. The vessel was sealed and the contents were stirred for 2 hr at room temperature. The hydrogen fluoride was removed on the aspirator. The residue was triturated with 300 -mol of dichloromethane. The dichloromethane solution was treated with sodium fluoride powder, filtered and concentrated under vacuum to 0.80 g of yellow oil. The product was analyzed by glpc (as in Example 1) as a mixture of 4-(difluoromethyl)nitrobenzene (50%) and 4-(fluoromethyl)nitrobenzene (50%).

EXAMPLE 23

Methyl 4-(fluoromethyl)benzenesulfonate and Methyl 4-(difluoromethyl)benzenesulfonate from Methyl 4-toluenesulfonate

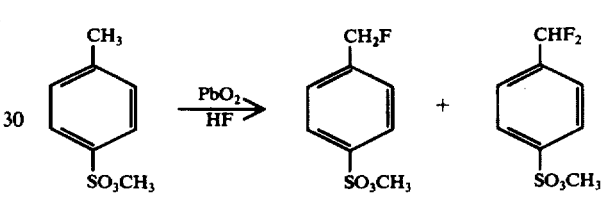

A 200-ml polychlorotrifluoroethylene vessel was charged with 2.42 g (0.013 mole) of methyl 4-toluenesulfonate and 7.2 g 80.03 mole) of lead dioxide. The vessel was cooled in liquid nitrogen, evacuated and charged with 30 ml hydrogen fluoride. The vessel was sealed, immersed in an ice water bath and the contents were stirred for 3 hr. The hydrogen fluoride was removed by aspirator vacuum. The residue was triturated with 3 × 100-ml portions of dichloromethane. The combined dichloromethane solutions were treated with 20 g sodium fluoride powder, filtered and concentrated under vacuum to a brown oil. Distillation of the oil gave 1.45 g of clear oil bp 115°-125° (0.7mm). Glpc analysis of the oil using the column of Example 1 and an oven temperature of 70° showed two peaks with retention times of 6 min and 8.8 min and relative areas of 55% and 45%. These materials were identified by gc-ms as methyl 4-(difluoromethyl)benzene-sulfonate and methyl 4-(fluoromethyl)benzenesulfonate, respectively. The mixture was also analyzed by $^1$H nmr, δ 3.78 (s) and 3.80 (s) OCH$_3$, 5.52 (d, J = 47 Hz) CH$_2$F, and 6.79 ppm (t, H = 56 Hz) CHF$_2$.

Following the general procedures disclosed above, the starting compounds shown in Column A of Table I when reacted with HF and the metal oxide shown in Column B, give the products listed in Columns C and D.

Table I

| Example | A. Starting Compound | B. Metal Oxide | C. (Fluoromethyl) Compound | D. (Difluoromethyl) Compound |
|---|---|---|---|---|
| 24 | 4-CH$_3$C$_6$H$_4$CF$_3$ | PbO$_2$ | 4-FCH$_2$C$_6$H$_4$CF$_3$ | 4-F$_2$CHC$_6$H$_4$CF$_3$ |
| 25 | 4-CH$_3$C$_6$H$_4$CO$_2$H | NiO$_2$ | 4-FCH$_2$C$_6$H$_4$CO$_2$H | 4-F$_2$CHC$_6$H$_4$CO$_2$H |
| 26 | 4-CH$_3$C$_6$H$_4$CONH$_2$ | NiO$_2$ | 4-FCH$_2$C$_6$H$_4$CONH$_2$ | 4-F$_2$CHC$_6$H$_4$CONH$_2$ |
| 27 | 4-CH$_3$C$_6$H$_4$CO$_2$CH$_3$ | NiO$_2$ | 4-FCH$_2$C$_6$H$_4$CO$_2$CH$_3$ | 4-F$_2$CHC$_6$H$_4$CO$_2$CH$_3$ |
| 28 | 4-CH$_3$C$_6$H$_4$COC$_6$H$_5$ | NiO$_2$ | 4-FCH$_2$C$_6$H$_4$COC$_6$H$_5$ | 4-F$_2$CHC$_6$H$_4$COC$_6$H$_5$ |
| 29 | 3-CH$_3$C$_6$H$_4$NO$_2$ | NiO$_2$ | 3-FCH$_2$C$_6$H$_4$NO$_2$ | 3-F$_2$CHC$_6$H$_4$NO$_2$ |
| 30 | 2-CH$_3$C$_6$H$_4$NO$_2$ | NiO$_2$ | 2-FCH$_2$C$_6$H$_4$NO$_2$ | 2-F$_2$CHC$_6$H$_4$NO$_2$ |
| 31 | 2-ClCH$_2$C$_6$H$_4$NO$_2$ | PbO$_2$ | — | 2-F$_2$CHC$_6$H$_4$NO$_2$ |
| 32 | 3-BrCH$_2$C$_6$H$_4$NO$_2$ | PbO$_2$ | — | 3-F$_2$CHC$_6$H$_4$NO$_2$ |
| 33 | 4-FCH$_2$C$_6$H$_4$NO$_2$ | NiO$_2$ | — | 4-F$_2$CHC$_6$H$_4$NO$_2$ |
| 34 | 4-ICH$_2$C$_6$H$_4$CO$_2$H | PbO$_2$ | — | 4-F$_2$CHC$_6$H$_4$CO$_2$H |
| 35 | 3-C$_2$H$_5$C$_6$H$_4$NO$_2$ | PbO$_2$ | 3-(CH$_3$CHF)C$_6$H$_4$NO$_2$ | 3-(CH$_3$CF$_2$)C$_6$H$_4$NO$_2$ |
| 36 | 2-C$_3$H$_7$C$_6$H$_4$NO$_2$ | PbO$_2$ | 2-(CH$_3$CH$_2$CH$_2$CHF)C$_6$H$_4$NO$_2$ | 2-(CH$_3$CH$_2$CH$_2$CF$_2$)C$_6$H$_4$NO$_2$ |
| 37 | 4-C$_2$H$_5$C$_6$H$_4$CO$_2$H | NiO$_2$ | 4-(CH$_3$CHF)C$_6$H$_4$CO$_2$H | 4-(CH$_3$CF$_2$)C$_6$H$_4$CO$_2$H |
| 38 | 4-CH$_3$-3-NO$_2$C$_6$H$_3$CO$_2$H | PbO$_2$ | 4-FCH$_2$-3-NO$_2$—C$_6$H$_3$CO$_2$H | 4-F$_2$CH-3-NO$_2$—C$_6$H$_3$CO$_2$H |
| 39 | 4-CH$_3$-3-ClC$_6$H$_3$NO$_2$ | PbO$_2$ | 4-FCH$_2$-3-ClC$_6$H$_3$NO$_2$ | 4-F$_2$CH-3-ClC$_6$H$_3$NO$_2$ |
| 40 | 2,4-(NO$_2$)$_2$C$_6$H$_3$CH$_3$ | NiO$_2$ | 2,4-(NO$_2$)$_2$C$_6$H$_3$CH$_2$F | 2,4-(NO$_2$)$_2$C$_6$H$_3$CHF$_2$ |
| 41 | 2-Br-4-NO$_2$C$_6$H$_3$CH$_3$ | PbO$_2$ | 2-Br-4-NO$_2$C$_6$H$_3$CH$_2$F | 2-Br-4-NO$_2$C$_6$H$_3$CHF$_2$ |
| 42 | 2-F-4-HO$_2$CC$_6$H$_3$CH$_3$ | PbO$_2$ | 2-F-4-HO$_2$CC$_6$H$_3$CH$_2$F | 2-F-4-HO$_2$CC$_6$H$_3$CHF$_2$ |
| 43 | 4-CH$_3$C$_6$H$_4$SO$_2$N(CH$_3$)$_2$ | PbO$_2$ | 4-FCH$_2$C$_6$H$_4$SO$_2$N(CH$_3$)$_2$ | 4-F$_2$CHC$_6$H$_4$SO$_2$N(CH$_3$)$_2$ |
| 44 | 2-NO$_2$-4-HO$_2$CC$_6$H$_3$CH$_3$ | PbO$_2$ | 2-NO$_2$-4-HO$_2$CC$_6$H$_3$CH$_2$F | 2-NO$_2$-4-HO$_2$CC$_6$H$_3$CHF$_2$ |
| 45 | 2-NO$_2$-1,4-(CH$_3$)$_2$C$_6$H$_3$ | PbO$_2$ | 2-NO$_2$-1,4-(FCH$_2$)$_2$C$_6$H$_3$ | 2-NO$_2$-1,4-(F$_2$CH)$_2$C$_6$H$_3$<br>2-NO$_2$-1-(FCH$_2$)-4-(F$_2$CH)C$_6$H$_3$<br>2-NO$_2$-1-(F$_2$CH)-4-(FCH$_2$)C$_6$H$_3$ |
| 46 | 4-NO$_2$-1,2-(CH$_3$)$_2$C$_6$H$_3$ | NiO$_2$ | 4-NO$_2$-1,2-(FCH$_2$)$_2$C$_6$H$_3$ | 4-NO$_2$-1,2-(F$_2$CH)$_2$C$_6$H$_3$<br>4-NO$_2$-1-(F$_2$CH)-2-(FCH$_2$)C$_6$H$_3$<br>4-NO$_2$-1-FCH$_2$)-2-(F$_2$CH)C$_6$H$_3$ |
| 47 | 4-HO$_2$C-1,3-(CH$_3$)$_2$C$_6$H$_3$ | PbO$_2$ | 4-HO$_2$C-1,3-(FCH$_2$)$_2$C$_6$H$_3$ | 4-HO$_2$C-1,3-(F$_2$CH)$_2$C$_6$H$_3$<br>4-HO$_2$C-1-(FCH$_2$)-3-(F$_2$CH)C$_6$H$_3$<br>4-HO$_2$C-1-(F$_2$CH)-3-(FCH$_2$)C$_6$H$_3$ |
| 48 | 1,4-(HO$_2$C)$_2$-2-CH$_3$C$_6$H$_3$ | PbO$_2$ | 1,4-(HO$_2$C)$_2$-2-(FCH$_2$)C$_6$H$_3$ | 1,4-(HO$_2$C)$_2$-2-(F$_2$CH)C$_6$H$_3$ |
| 49 | 2-CH$_3$-4-ClC$_6$H$_3$COCH$_3$ | PbO$_2$ | 2-FCH$_2$-4-ClC$_6$H$_3$COCH$_3$ | 2-F$_2$CH-4-ClC$_6$H$_3$COCH$_3$ |
| 50 | 2-O$_2$N-4-CH$_3$C$_6$H$_3$C$_6$H$_3$ | PbO$_2$ | 2-O$_2$N-4-(FCH$_2$)C$_6$H$_3$C$_6$H$_3$ | 2-O$_2$N-4-(F$_2$CH)C$_6$H$_3$C$_6$H$_3$ |
| 51 | [2-methyl-anthraquinone structure] | PbO$_2$ | [2-fluoromethyl-anthraquinone structure] | [2-difluoromethyl-anthraquinone structure] |
| 52 | [1,4-dimethyl-anthraquinone structure] | PbO$_2$ | [1,4-bis(fluoromethyl)-anthraquinone structure] | [1,4-bis(difluoromethyl)-anthraquinone structures] |
| 53 | 4-CH$_3$C$_6$H$_4$CO$_2$C(CH$_3$)$_3$ | PbO$_2$ | 4-FCH$_2$C$_6$H$_4$CO$_2$C(CH$_3$)$_3$ | 4-F$_2$CHC$_6$H$_4$CO$_2$C(CH$_3$)$_3$ |
| 54 | 4-CH$_3$C$_6$H$_4$CO$_2$C$_6$H$_5$ | PbO$_2$ | 4-FCH$_2$C$_6$H$_4$CO$_2$C$_6$H$_5$ | 4-F$_2$CHC$_6$H$_4$CO$_2$C$_6$H$_5$ |
| 55 | 4-CH$_3$C$_6$H$_4$SO$_2$OC$_2$H$_5$ | PbO$_2$ | 4-FCH$_2$C$_6$H$_4$SO$_2$OC$_2$H$_5$ | 4-F$_2$CHC$_6$H$_4$SO$_2$OC$_2$H$_5$ |
| 56 | 4-CH$_3$C$_6$H$_4$SO$_2$OC$_6$H$_5$ | PbO$_2$ | 4-FCH$_2$C$_6$H$_4$SO$_2$OC$_6$H$_5$ | 4-F$_2$CHC$_6$H$_4$SO$_2$OC$_6$H$_5$ |

The mono- and difluorinated products are useful intermediates in a variety of areas. In general, the (fluoromethyl)aromatic compounds (benzyl fluorides) readily undergo Friedel-Crafts reaction with a variety of aromatic compounds to give diphenylmethane derivatives (J. Bernstein, J. S. Roth, and W. T. Miller, J. Amer. Chem. Soc., 70, 2310 (1948)). They undergo ethanolysis, hydrolysis and acetolysis to benzyl ethers, alcohols and acetates, respectively (Bernstein et al., loc. cit.). 4,4'-Dinitrostilbene epoxide can be prepared in high yield from 4-(fluoromethyl)nitrobenzene (4-nitrobenzyl fluoride) (F. M. Fouad and P. G. Farrell, *J. Org. Chem.*, 40, 3881 (1975)). (Difluoromethyl)aromatic compounds (benzal fluorides) are useful intermediates for the synthesis of a variety of biologically active compounds. Thus, 3-(difluoromethyl)nitrobenzene (m-nitrobenzal fluoride) can be reduced to 3-(difluoromethyl)aniline (m-aminobenzal fluoride) which is a pesticide intermediate (O. Scherer and H. Hartmut, West German Pat. No. 2,032,565, Jan. 5, 1972). 3- and 4-(Difluoromethyl)nitrobenzenes (m- and p-nitrobenzal fluorides) can be converted to ureas which are selective herbicides for cotton (French Pat. No. 2,013,336, Apr. 3, 1970). 4-(Difluoromethyl)benzoic acid, 4-(difluoromethyl)benzamide, and 4-(difluoromethyl)benzonitrile are intermediates for preparing pharmaceuticals (F. Mathey and J. Bensoam, French Pat. No. 2,254,558, July 11, 1975). The difluoromethyl group can be hydrolyzed to an aldehyde. Thus, 4-(difluoromethyl)(trifluoromethyl)benzene ($\alpha,\alpha,\alpha',\alpha'$, pentafluoro-p-xylene) is converted to 4-(trifluoromethyl)benzaldehyde which is a useful intermediate for dyes, fungicides, insecticides and pharmaceutical products (British Pat. No. 466,007, May 20, 1937 to I. G. Farbenindustrie A.

G.). The fluoromethyl compounds of this invention may also be regarded as chemical intermediates to the above-mentioned difluoromethyl compounds.

I claim:
1. The fluorination process which consists essentially in reacting under substantially anhydrous conditions one mode of an aromatic compound of the formula

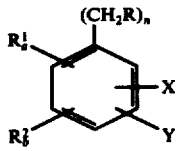

wherein
$n$ is 1 to 3;
$a$ and $b$ are each 0 or 1 with the proviso that $n$ is at least 1 and the sum of $n$, $a$ and $b$ does not exceed 3;
R is H, alkyl of 1-3 carbons or Z in which Z is F, Cl, Br or I;
$R^{21}$ and $R^2$ are H or phenyl or together are 1,2-phthaloyl;
X and Y are H, $NO_2$, COOH, CHO, $CONH_2$, $COOR^3$, $COR_3$, $SO_3H$, $CF_3$, CN, $SO_2OR^3$, $SO_2NR_2^3$, F, Cl, Br or I with the proviso that only one of X and Y can be H, F, Cl, Br or I; and
$R^3$ is alkyl of 1-4 carbons or phenyl;
with at least three moles of HF and at least one mole of a metal oxide selected from the group consisting of lead dioxide and nickel dioxide at a temperature range of about $-30°$ to about $+80°$ C for about 10 minutes to about 22 hours with the proviso that when nickel dioxide is used it is the last reactant added, and recovering an aromatic compound having a mono- or difluorinated benzylic carbon compound.

2. The process of claim 1 where the metal oxide is lead dioxide.

3. The process of claim 1 where the metal oxide is nickel dioxide.

4. The process of claim 1 where R is H or $CH_3$.

5. The process of claim 1 where R is Z and Z is F or Cl.

6. The process of claim 1 wherein $R^1$ and $R^2$ are each H.

7. The process of claim 1 where X is H and Y is $NO_2$, COOH, $CONH_2$, $COOC_2H_5$, CHO, $COC_6H_5$, CN, $SO_3H$ or $SO_2OCH_3$.

8. The process of claim 1 where X and Y are each $NO_2$.

9. The process of claim 1 where HF is used in excess of three moles per mole of aromatic compound.

10. The process of claim 1 where HF is 2 to 20 times the weight of metal oxide used.

11. The process of claim 1 where the metal oxide is used in excess of one mole per mole of aromatic compound.

12. The process of claim 1 where the temperature is 0° to 25° C.

13. The process of claim 1 where the starting aromatic compound is nitrotoluene.

14. The process of claim 1 where the starting aromatic compound is 4-nitrotoluene.

15. The process of claim 1 where the starting aromatic compound is methylbenzoic acid.

16. The process of claim 1 where the starting aromatic compound is methylbenzaldehyde.

17. The process of claim 1 where the starting aromatic compound is ethylnitrobenzene.

18. The process of claim 1 where the starting aromatic compound is methylbenzamide.

19. The process of claim 1 where the starting aromatic compound is ethyl methylbenzoate.

20. The process of claim 1 where the starting aromatic compound is dinitrotoluene.

21. The process of claim 1 where the starting aromatic compound is (chloromethyl)nitrobenzene.

22. The process of claim 1 where the starting aromatic compound is methylbenzophenone.

23. The process of claim 1 where the starting aromatic compound is methylbenzonitrile.

24. The process of claim 1 where the starting aromatic compound is toluenesulfonic acid.

25. The process of claim 1 where the starting aromatic compound is dimethylnitrobenzene.

26. The process of claim 1 where the starting aromatic compound is methyl toluenesulfonate.

* * * * *